Aug. 25, 1964 F. L. RYPCZYNSKI Plant Pat. 2,440
APPLE TREE
Filed April 17, 1962
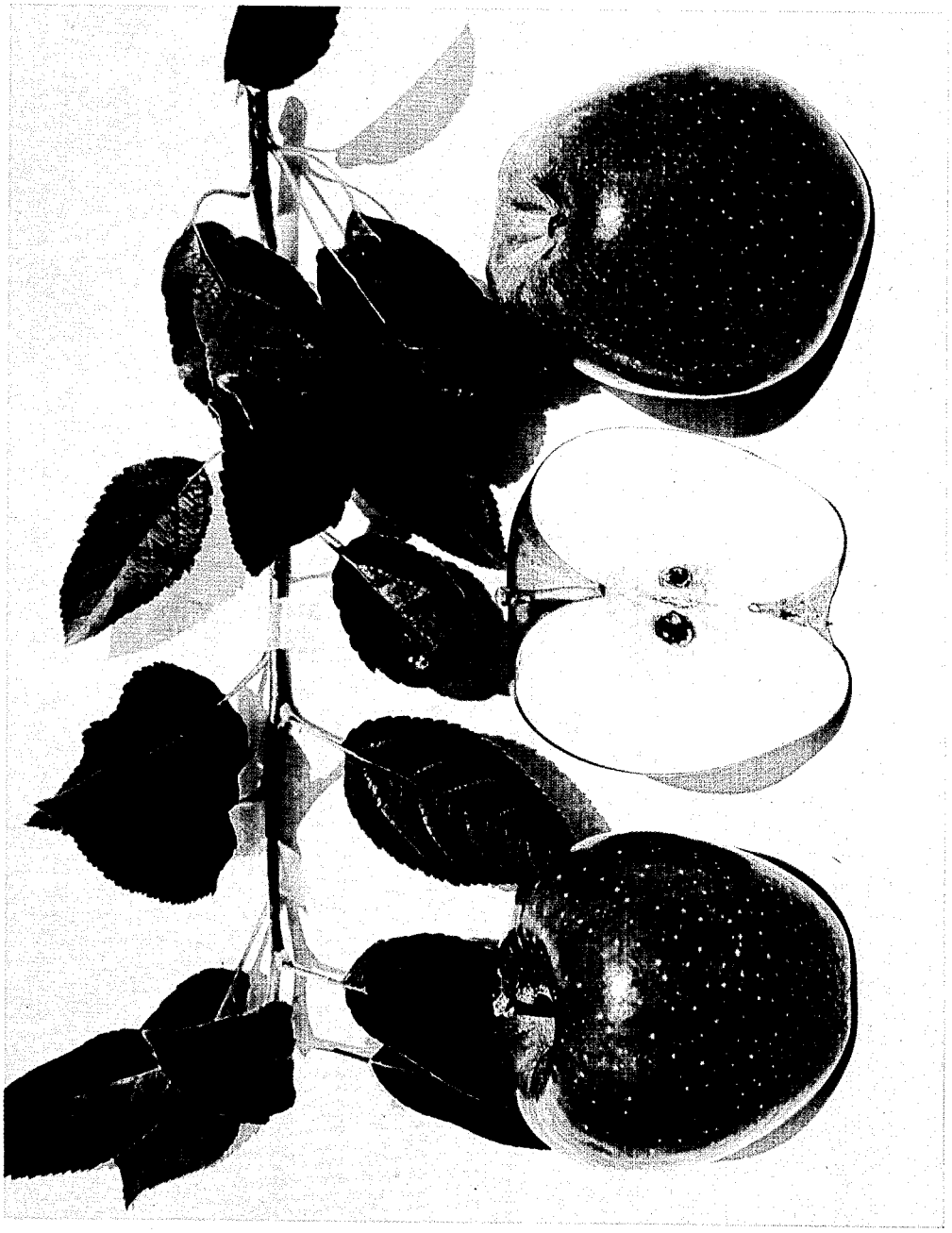
Inventor.
Frank L. Rypczynski
By: Robb & Robb
Attorneys.

United States Patent Office

Plant Pat. 2,440
Patented Aug. 25, 1964

2,440
APPLE TREE

Frank L. Rypczynski, Hood River, Oreg., assignor to Stark Bro's Nurseries & Orchards Company, Louisiana, Mo., a corporation of Missouri Filed Apr. 17, 1962, Ser. No. 188,290
1 Claim. (Cl. Plt.—35)

The present invention relates to a new and distinct variety of apple tree which was discovered by me as a limb sport of the variety commonly known as the Mood Apple (unpatented), which is extensively distributed and sold by the assignee hereof under the registered trademark "Starking." My discovery was made in my cultivated orchard which is located at Hood River, Oregon.

At the time of my discovery, I was growing in my orchard aforesaid trees of the Mood Apple variety, and while engaged in routine care of the orchard, my attention was attracted to one tree which had fruit on one limb thereof which appeared to be distinctly different from the fruit on the remainder of the tree and on other trees of the same variety in the same orchard. Closer and prolonged observation of this particular tree convinced me that the limb bearing the unusual fruit aforementioned, was the result of a bud sport, and I thereupon took prompt steps to preserve the limb and to keep it under close observation.

In due course, I asexually reproduced the new sport by budding, as performed by me in my orchard aforesaid, and the progeny resulting therefrom, together with continued observations and tests of the original limb sport on the mother tree over a period of years, have conclusively demonstrated that the sport is definitely a new and distinct variety, as particularly evidenced by the following unique combination of characteristics which are outstanding therein and which distinguish the sport from the standard Mood Apple variety, as well as from all other varieties of which I am aware:

(1) A general resemblance of the fruit to the fruit of the Mood Apple variety, but having a much earlier fruit coloring habit and a habit of developing a full red color approximately 30 days before maturity, and somewhat earlier than the variety known as "Red King" (Plant Patent No. 1,411);

(2) A striped fruit coloring pattern, with the stripes being narrower and more obscure than those of the variety known as "Red King" (Plant Patent No. 1,411), which is another sport of the Mood Apple; and (3) A substantially solid red over all color effect of the fruit color, with relatively obscure stripes of a darker red shade which are hardly nocticeable at maturity.

The accompanying drawing shows typical specimens of the foliage as borne on a typical branch section, as well as typical specimens of the fruit, and with one of the fruit specimens being shown in cross-section, all as depicted in color as nearly true as it is reasonably possible to make the same in a color illustration of this character.

The following is a detailed description of my new variety, with color terminology in accordance with Munsell Color Chart (hereinafter abbreviated as "Munsell"), and the Horticulural Colour Guide (hereinafter abbreviated as "HCG"), as indicated, except where general color terms of ordinary dictionary signficance are obvious:

Locality where grown and observed: Hood River, Oregon.
Dates of first and last pickings: About September 25 and about October 5, respectively.
Tree: Large size; vigorous; spreading; tall; vase-formed; rapid growing; hardy: productive; regular bearer.
*Trunk.*—Medium stocky; smooth.
*Branches.* — Medium thickness; smooth; little-branched. Color — Moderate Reddish Brown, Plate 7.5R 3/6 (Munsell). Lenticels—medium-few; medium small.
*Leaves.*—Medium large; medium width; medium length; ovate; taper-pointed; thick; rugose. Average length—3½ inches. Average width—2⅛ inches. Color—Ivy Green, Plate 0960, page 187, vol. 2 (HCG). Margin—coarsely serrate. Petiole—medium long (1 inch); thick.

Flowers:
*Dates of first and full bloom.*—About May 1 and about May 10, respectively; medium early as compared with other varieties.
*Color.*—White, with Light Purplish Pink, Plate 7.5RP 8/5 (Munsell) areas on lower (outer) surface near base.

Fruit:
*Maturity when described.*—Eating ripe.
*Size.*—Uniform. Axial diameter—about 3⅛ inches. Transverse diameter—about 3 inches.
*Form.*—Conical; angular.
*Cavity.*—Symmetrical; flaring; acute; even; pubescent toward apex. Depth—about ¾ inch. Breadth—about 1¼ inches. Markings: color—Dark Greenish Yellow, Plate 7.5Y 6/7 (Munsell).
*Basin.*—Symmetrical; rounded; wide-furrowed; pubescent. Depth—about ¼ inch. Breadth—about 1 inch. Markings—none.
*Stem.*—Stout; pubescent. Length—from about 1 inch to 1⅜ inches. Breadth—about 3/32 inch.
*Calyx.*—Closed; segments persistent; broadly lanceolate; acute; about ¼ inch long; approximate; prostrate; reflexed from base at apex; both outer and inner surfaces pubescent.
*Skin.*—Thick; tough; smooth; glossy; waxed. Dots—obscure, many, small, depressed, circular; color—Yellowish Pink, Plate 7.5R 9/4 (Munsell); distribution—distributed over entire surface, but more numerous toward base. Ground color—Red, Plate 2.5R 4/10 (Munsell). Markings—striped; bright; color—red, Plate 10RP 3/9 (Munsell).
*Bloom.*—Wanting.
*Scarfskin.*—Wanting.
*General color effect.*—Striped, deep red all over.
*Flesh.*—Rather juicy. Color—satiny white, with greenish tint. Texture—firm; fine; crisp. Flavor—subacid; mild; rich. Aroma—distinct. Quality—good.
*Core.*—Distant. Bundle area—medium small; cordate; symmetrical at base; acute at base. Halves of core—equal. Bundles—inconspicuous; color—Green, Plate 2,5GY 9/8 (Munsell). Core lines—clasping. Carpellary area—indistinct; small. Calyx tube—pubescent toward base, funnel form, stem of funnel long; depth of tube to shoulder—about ⅜ inch; entire depth—about ½ inch. Styles—present. Stamens—in one distinct whorl; basal. Seed cells—axile, open; cell walls—thin, tough, length—about 13/16 inch; breadth—about 5/16 inch; longitudinal section—obovate; cross section—narrow; surface—fissured, tufted.

Seeds:
*Average number.*—11, usually with 3 seeds per cell. Length—from about ¼ inch to ⅜ inch. Breadth—about 3/16 inch.
*Color.*—Moderate Brown, Plate 7.5YR 4/5.

Use: Market; dessert.
Keeping quality: Medium-good; about 100 days in ordinary storage.

I claim:

A new and distinct variety of apple tree, substantially as herein shown and described, characterized particularly as to novelty by the unique combination of a general resemblance of the fruit to that of the Mood Apple variety (unpatented), but having a much earlier coloring habit, with the coloring developing to a full red color approximately thirty days before maturity, said fruit coloring having a striped pattern, with the stripes narrower and more obscure than those of the variety "Red King" (Plant Patent No. 1,411), and the over all fruit color effect being substantially solid red with obscure stripes of a darker red shade at maturity.

No references cited.